US010548751B2

(12) United States Patent
You et al.

(10) Patent No.: US 10,548,751 B2
(45) Date of Patent: Feb. 4, 2020

(54) STENT PLACEMENT DEVICE

(71) Applicant: OXFORD UNIVERSITY INNOVATION LIMITED, Botley, Oxford (GB)

(72) Inventors: Zhong You, Oxford (GB); Jiayao Ma, Oxford (GB); James Byrne, Oxford (GB)

(73) Assignee: OXFORD UNIVERSITY INNOVATION LIMITED, Botley, Oxford (GB)

( * ) Notice: Subject to any disclaimer, the term of this patent is extended or adjusted under 35 U.S.C. 154(b) by 144 days.

(21) Appl. No.: 15/119,303

(22) PCT Filed: Feb. 16, 2015

(86) PCT No.: PCT/GB2015/050427
§ 371 (c)(1),
(2) Date: Aug. 16, 2016

(87) PCT Pub. No.: WO2015/121678
PCT Pub. Date: Aug. 20, 2015

(65) Prior Publication Data
US 2017/0007433 A1 Jan. 12, 2017

(30) Foreign Application Priority Data
Feb. 17, 2014 (GB) .................................. 1402758.5

(51) Int. Cl.
*A61F 2/95* (2013.01)
*A61F 2/966* (2013.01)
(52) U.S. Cl.
CPC ...... *A61F 2/966* (2013.01); *A61F 2002/9517* (2013.01)

(58) Field of Classification Search
CPC .. A61F 2/966; A61F 2002/9517; A61F 2/954; A61F 2/958; A61F 2/97;
(Continued)

(56) References Cited

U.S. PATENT DOCUMENTS 6,786,918 B1 9/2004 Krivoruchko et al.
2002/0183827 A1 12/2002 Derus et al.
(Continued)

FOREIGN PATENT DOCUMENTS

CN 101404960 A 4/2009
CN 103052365 A 4/2013
(Continued)

OTHER PUBLICATIONS

Japanese Office Action regarding Application No. 2016-569107 dated Nov. 13, 2018. Office Action Summary provided by JA Kemp.

*Primary Examiner* — Erich G Herbermann
(74) *Attorney, Agent, or Firm* — Harness, Dickey & Pierce, P.L.C.

(57) ABSTRACT

A stent placement assembly is disclosed. In disclosed example, the stent placement assembly comprises a stent placement assembly, comprising: a holding catheter comprising a longitudinal lumen for receiving a stent, and an output orifice at a distal end; a stopper member positioned within said lumen and moveable longitudinally relative thereto, the stopper member being configured to engage with the stent in order to restrict movement of the stent in a proximal direction; a first anchor member coupled to the holding catheter at a proximal end thereof; a second anchor member coupled to the stopper member at a proximal end thereof; and a displacement device comprising a first engagement member and a second engagement member, the first and second engagement members being configured to engage respectively with the first and second anchor members in such a way that displacement of the first engagement (Continued)

member relative to the second engagement member causes a corresponding displacement between the first and second anchor members, wherein: the displacement device further comprises: a handle rigidly connected to one of the first and second engagement members and a user actuatable displacement mechanism configured to be actuatable by a user while gripping the handle, the actuation being such as to cause displacement of the other one of the first and second engagement members relative to the handle thereby causing the holding catheter to withdraw in a proximal direction relative to the stopper member and thereby release the stent through the output orifice.

7 Claims, 2 Drawing Sheets

(58) Field of Classification Search
CPC ...... A61F 2002/9505; A61F 2002/9522; A61F 2002/9534; A61F 2/95; A61F 2/962; A61F 2002/9511; A61F 2002/9528; A61F 2002/9583; A61F 2002/9586; A61F 2002/9665
See application file for complete search history.

(56) References Cited

U.S. PATENT DOCUMENTS

| | | | |
|---|---|---|---|
| 2009/0030496 A1 | 1/2009 | Kaufmann et al. | |
| 2011/0307049 A1 | 12/2011 | Kao | |
| 2012/0029067 A1 | 2/2012 | Dou et al. | |
| 2012/0185031 A1* | 7/2012 | Ryan | A61F 2/966 623/1.12 |
| 2012/0238806 A1 | 9/2012 | Mangiardi et al. | |
| 2014/0277345 A1* | 9/2014 | Havel | A61F 2/966 623/1.11 |

FOREIGN PATENT DOCUMENTS

| | | |
|---|---|---|
| CN | 103096825 A | 5/2013 |
| CN | 103096838 A | 5/2013 |
| CN | 103356316 A | 10/2013 |
| DE | 10-2006-004123 A1 | 8/2007 |
| EP | 2604231 A2 | 6/2013 |
| JP | 2007195963 A | 8/2007 |
| JP | 2008212693 A | 9/2008 |
| WO | WO-2007-029242 A1 | 3/2007 |
| WO | WO-2007-098232 A2 | 8/2007 |

* cited by examiner

STENT PLACEMENT DEVICE

CROSS REFERENCE TO RELATED APPLICATIONS

This application is a U.S. National Phase Application under 35 U.S.C. 371 of International Application No. PCT/GB2015/050427 filed on Feb. 16, 2015 and published as WO 2015/121678 A1 on Aug. 20, 2015. This application claims priority to British Application No. 1402758.5 filed on Feb. 17, 2014. The entire disclosures of all of the above applications are incorporated herein by reference.

The invention relates to a stent placement device that is configured to facilitate precise deployment of a stent into a human or animal body.

Medical endoprostheses, commonly referred to as stents, have been widely used for minimum-invasive treatment of diseased blood vessels. Stents may be used to keep a blood vessel open, for example, or may redirect flow away from an aneurysm.

Self-expanding stents may be mechanically compressed springs which expand when released. Such stents may be constructed from shape-memory materials such as Nitinol. Stents used in the vascular system may be implanted transluminally during or following percutaneous transluminal angioplasty. The stents may be inserted into the vessel, positioned across the treatment area and then allowed to self-expand.

A known catheter assembly for delivering a self-expanding stent consists of an outer holding catheter in which the stent is loaded at a tip. The holding catheter may be provided to prevent premature expansion at body temperatures for heat induced shape memory stents or to contain mechanically restrained or stress induced shape memory stents. An inner stopper may be placed coaxially with the stent in the outer holding catheter to prevent the stent from moving in the proximal direction (longitudinally towards the operator of the stent) when deployed. Upon deployment, the inner stopper is held steady (for example via a connecting wire) and the holding catheter is pulled back to unsheath the stent. This procedure requires a surgeon to operate double handedly, and it is challenging to synchronize the movement of both hands to achieve a precise placement of a stent. A high level of skill and experience is needed for this operation.

U.S. Pat. No. 6,786,918 B1 discloses a stent placement device in which a handle is provided with a slot and a knob that can move longitudinally within the slot. The knob is coupled to an outer holding catheter such that movement of the knob imparts movement to the outer holding catheter. The device allows a surgeon to deploy a stent one handedly. However, the arrangement is complex and requires extensive adaptation of the outer holding catheter and inner stopper relative to standard arrangements that are configured for two handed operation.

An object of the present invention is to provide a stent placement device which can be operated more easily, for example with less need for skill and/or experience, which allows more precise and reliable placement of the stent, and/or which can be applied to existing stent placement apparatuses within minimal adaptation.

According to an aspect of the invention, there is provided a stent placement assembly, comprising: a holding catheter comprising a longitudinal lumen for receiving a stent, and an output orifice at a distal end; a stopper member positioned within said lumen and moveable longitudinally relative thereto, the stopper member being configured to engage with the stent in order to restrict movement of the stent in a proximal direction; a first anchor member coupled to the holding catheter at a proximal end thereof; a second anchor member coupled to the stopper member at a proximal end thereof; and a displacement device comprising a first engagement member and a second engagement member, the first and second engagement members being configured to engage respectively with the first and second anchor members in such a way that displacement of the first engagement member relative to the second engagement member causes a corresponding displacement between the first and second anchor members, wherein: the displacement device further comprises a handle rigidly connected to one of the first and second engagement members and a user actuatable displacement mechanism configured to be actuatable by a user while gripping the handle, the actuation being such as to cause displacement of the other one of the first and second engagement members relative to the handle thereby causing the holding catheter to withdraw in a proximal direction relative to the stopper member and thereby release the stent through the output orifice.

Thus, an arrangement is provided which facilitates accurate and reliable placement of a stent by a surgeon. In comparison with prior art devices which require two handed operation by a surgeon, the present invention is an improvement because it can be operated using a single hand. In comparison with prior art which allows for single handed operation, the present invention provides a mechanically simpler solution and one which can be easily disengaged from the catheter assembly. Furthermore, minimal adaptation is needed to established catheter assemblies for stent deployment.

In an embodiment, the displacement device is configured to allow the engagement with the catheter assembly to be detachable. This facilitates use of the stent placement assembly by a surgeon because it is not necessary to have the displacement device present when it is not needed.

In an embodiment, a movement transducer is provided for transforming movement of an actuator member imparted by a user into a movement of the first or second engagement member. The movement transducer may optionally be such as to cause the movement of the actuator member to be different from the corresponding movement of the first and second engagement members. This can improve flexibility of the device and makes it easier for the surgeon to deploy the stent precisely and/or quickly, according to the application in question. The movement transducer may also improve the ergonomic qualities of the stent placement assembly by obviating the need for the movement of the actuator member to be parallel with the axis of the catheter assembly and/or of the same magnitude as the desired movement between the holding catheter and the stopper member.

According to an aspect of the invention, there is provided a kit for facilitating operation of a catheter assembly for deploying a stent that comprises a holding catheter comprising a longitudinal lumen for receiving the stent, the holding catheter having an output orifice at a distal end, and a stopper member positioned within said lumen and movable longitudinally relative thereto, the stopper member being configured to engage with the stent in order to restrict movement of the stent in a proximal direction, wherein the kit comprises: a first anchor member couplable to the holding catheter at a proximal end thereof: a second anchor member couplable to the stopper member at a proximal end thereof: and a displacement device comprising a first engagement member and a second engagement member, the first and second engagement members being configured to engage respectively with the first and second anchor members, when coupled to the holding catheter and the stopper member, in such a way that displacement of the first engagement member relative to the second engagement member causes a corresponding displacement between the first and second anchor members, wherein: the displacement assembly further comprises: a handle rigidly connected to one of the first and second engagement member and a user actuatable displacement mechanism configured to be actuatable by a user while gripping the handle, the actuation being such as to cause displacement of the other one of the first and second engagement members relative to the handle thereby causing the holding catheter to withdraw in a proximal direction relative to the stopper member and thereby release the stent through the output orifice.

According to an aspect of the invention, there is provided a displacement device for facilitating operation of a catheter assembly for deploying a stent, the catheter assembly comprising a holding catheter comprising a longitudinal lumen for receiving the stent, the holding catheter having an output orifice at a distal end, and a stopper member positioned within said lumen and moveable longitudinally relative thereto, the stopper member being configured to engage with the stent in order to restrict movement of the stent in a proximal direction, a first anchor member coupled to the holding catheter at a proximal end thereof, and a second anchor member coupled to the stopper member at a proximal end thereof, wherein the displacement device comprises: a first engagement member and a second engagement member, the first and second engagement members being configured to engage respectively with the first and second anchor members in such a way that displacement of the first engagement member relative to the second engagement member causes a corresponding displacement between the first and second anchor members; and a handle rigidly connected to one of the first and second engagement members and a user actuatable displacement mechanism configured to be actuatable by a user while gripping the handle, the actuation being such as to cause displacement of the other one of the first and second engagement members relative to the handle thereby causing the holding catheter to withdraw in a proximal direction relative to the stopper member and thereby release the stent through the output orifice.

Embodiments of the invention will now be described, by way of example only, with reference to the accompanying drawings in which corresponding reference symbols indicate corresponding parts, and in which.

Figure 1:
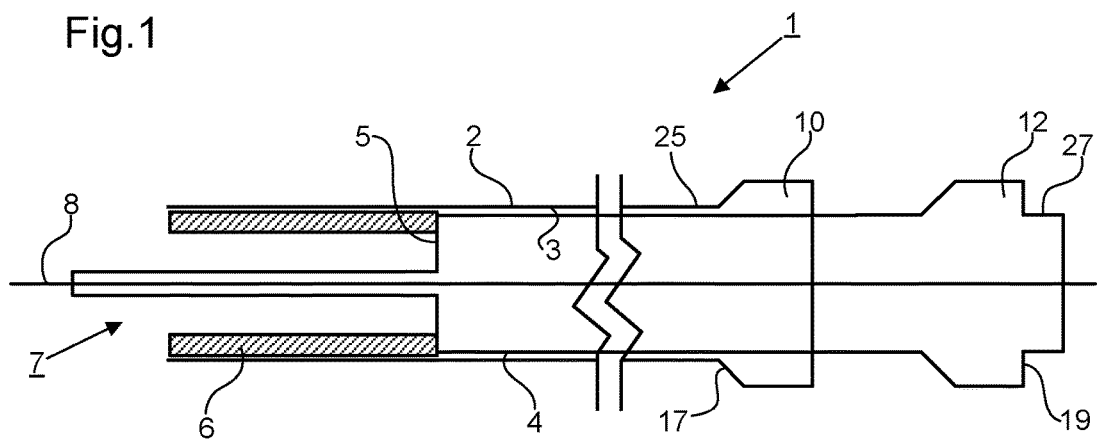
FIG. 1 depicts a catheter assembly for deploying a stent.

FIG. 1 is schematic sectional side view of a catheter assembly 1 for deploying a stent 6 within a human or animal body. In an embodiment, the stent 6 has a substantially cylindrical form. In an embodiment, the stent 6 is a self-expanding stent. In an embodiment of this type, the stent may be housed within the catheter assembly 1 in a radially constrained state and expands into a radially extended state when unsheathed or released from the catheter assembly 1. In an embodiment, the stent 6 is a flow diverter stent. In other embodiments, the stent may be configured to perform other functions, such as keeping a blood vessel open.

In the example shown in FIG. 1, the catheter assembly 1 comprises a holding catheter 2. The holding catheter 2 comprises a longitudinal lumen 3 that is configured to receive a stent 6. In an embodiment, the stent 6 is a self-expanding stent and is constrained radially by an inner surface of the lumen 3. The catheter assembly 1 further comprises a stopper member 4 which is positioned within the lumen 3 and movable longitudinally relative thereto. The stopper member 4 is configured to engage with the stent 6 in order to restrict movement of the stent 6 in a proximal direction. In the orientation of the figure, the proximal direction is to the right. The proximal direction refers more generally to the direction leading to the exterior of the patient along the axis of the catheter assembly 1. The proximal end of the catheter assembly 1 corresponds to an end which is usually outside of the patient's body. In the example shown, the stopper member 4 engages with the stent 6 via shoulders 5. However, this geometry is only exemplary and other geometries may be used to achieve the desired purpose of preventing proximal movement of the stent 6.

The holding catheter 2 comprises an output orifice 7 at a distal end thereof. Movement of the holding catheter 2 in a proximal direction relative to the stopper member 4 will lead to the stent 6 being driven out of the output orifice 7. When the stent 6 has completely left the output orifice 7 the stent 6 may extend radially into its final state and thereby be deployed within the location of interest within the body. The catheter assembly 1 may at this point be removed from the body.

The relative movement between the holding catheter 2 and the stopper member 4 may be achieved by a surgeon manipulating first and second anchor members 10 and 12. The first anchor member 10 is coupled (e.g. rigidly, relative to the longitudinal axis) to the holding catheter 2 at a proximal end of the holding catheter 2 (outside of the body). The second anchor member 12 is coupled (e.g. rigidly, relative to the longitudinal axis) to the stopper member 4 at a proximal end of the stopper member 4 (outside of the body).

In order to facilitate manipulation of the first and second anchor members 10 and 12, and particularly to allow manipulation to be carried out reliably and/or with a single hand, a displacement device 18 is provided.

Figure 2:
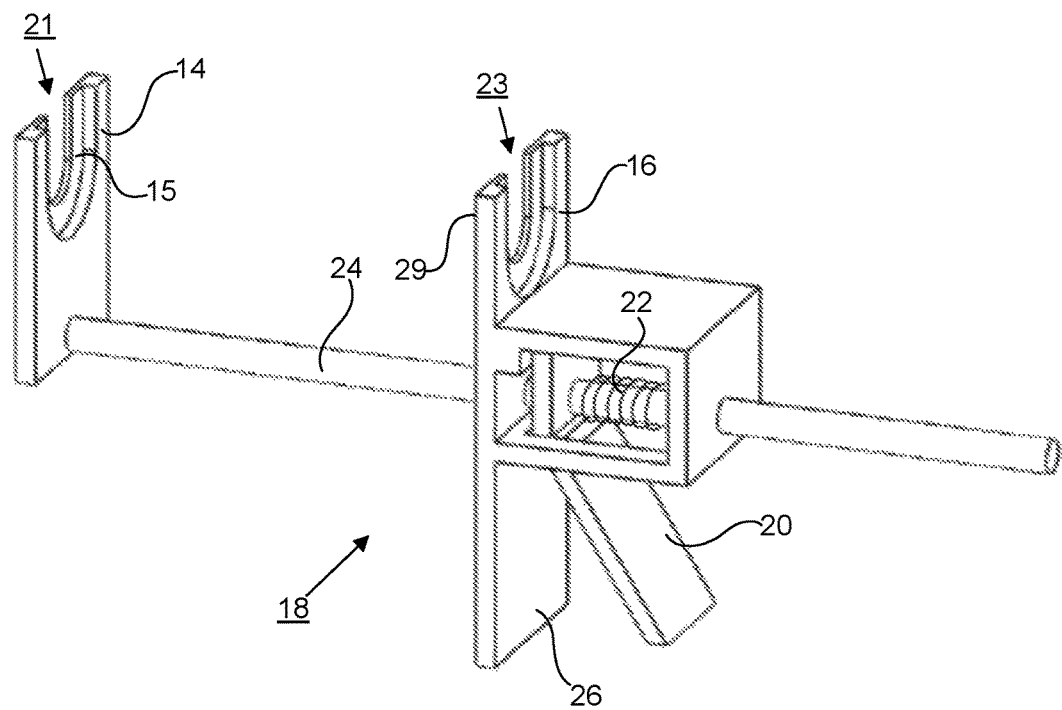
FIG. 2 depicts a stent placement assembly in which a displacement device comprises an actuator member and a movement transducer.

FIG. 2 is a schematic perspective view of an example displacement device 18. In this embodiment, the displacement device 18 comprises a first engagement member 14 and a second engagement member 16. The first and second engagement members 16 and 18 are configured to engage respectively with the first and second anchor members 10 and 12. In the example shown, the first engagement member 14 is configured to engage with the first anchor number 10 and the second engagement member 16 is configured to engage with the second anchor member 12. The engagement between the engagement members and the anchor members is such that displacement of the first engagement member 14 relative to the second engagement member 16 causes a corresponding displacement between the first and second anchor members 10 and 12. This may be achieved, for example, by arranging for the engagement to be such that there is no relative movement between the engagement member and its corresponding anchor member, at least in a longitudinal direction, when they are engaged with each other. In the example shown, it can be seen that this functionality is achieved by arranging for a region 25 distal of the first anchor member 10 to be inserted into a slot 21 in the first engagement member 14. In this state, a proximally facing edge 15 engages against a distal facing edge 17 of the first anchor member 10. Similarly, a region 27 proximal to the second anchor member 12 may be inserted into slot 23 of the second engagement member 16 and proximal facing edge 19 may engage against distal facing edge 29 of the second engagement member 16. In this way, when the displacement device causes movement of the first engagement member 14 towards the second engagement member 16, the fixed spatial relationship between the first anchor member 10 and the first engagement member 14 and between the second anchor member 12 and the second engagement member 16 ensures that a corresponding relative movement is transmitted to the holding catheter 2 relative to the stopper member 4.

In the embodiment shown, the displacement device 18 comprises a handle 26 (by which a user may grip the device) that is rigidly connected to the second engagement member 16. In other embodiments, the handle 26 may be rigidly connected to the first engagement member 14 instead of the second engagement member 16. The displacement device 18 further comprises a user actuatable displacement mechanism that is configured to be actuatable by a user while gripping the handle 26. The actuation causes displacement of the engagement member that is not rigidly connected to the handle relative to the handle. In the example shown, it is the first engagement member 14 which moves relative to the handle 26. The relative movement imparted to the first and second engagement members 14 and 16 causes a corresponding relative movement between the holding catheter 2 and the stopper member 4 and allows the holding member to be withdrawn in a proximal direction. This movement causes the stent 6 to be released through the output orifice 7.

In an embodiment, the engagement between the first and second engagement members 14 and 16 and the corresponding anchor members 10 and 12 is a detachable engagement. In the example shown, this is achieved by means of the slots 21 and 23 in the first and second engagement members 14 and 16, which allow the engagement members to be engaged or disengaged by moving them in the direction of the slots. Thus, the displacement device 18 may be kept separate to the catheter assembly 1 during use of the catheter assembly 1 which does not require the displacement device to be present. When it is necessary to deploy the stent out of the catheter assembly 1, the displacement device 18 may be brought into engagement. This arrangement therefore provides maximal flexibility and convenience for the surgeon.

In the example of FIG. 2, the user actuatable displacement mechanism comprises an actuator member 20 and a movement transducer for transforming movement of the actuator member 20 (imparted by the user, for example by squeezing the handle 26 and actuator member 20 between a palm and fingers) into a movement of the first or second engagement member (whichever happens not to be fixedly connected to the handle 26). The use of a movement transducer makes it possible for the action of the surgeon to be made maximally convenient for the surgeon and not be limited according to the actual movement required between the holding catheter 2 and the stopper member 4. The user actuatable displacement mechanism may be such that the imparted movement of the first or second engagement member follows a path that is different in shape and/or direction to the path followed by the actuator member 20. For example, the path of the actuator member may be curved (which may be convenient for the surgeon) while the path of the first or second engagement member may be linear (corresponding to the desired motion at the distal end of the catheter assembly 1).

In an embodiment, the user actuatable displacement mechanism is configured such that the length of the imparted movement of the first or second engagement members is different to the length of the corresponding path followed by the actuator member. For example, where it is desirable to achieve highly precise motion at the distal end of the catheter assembly 1 the user actuatable displacement mechanism may be configured such that the length of the path imparted to the first or second engagement member is significantly shorter than the corresponding path followed by the actuator member 26. Conversely, where it is desired to achieve rapid deployment of the stent 6 from the catheter assembly 1, the user actuatable displacement mechanism may be configured such that the length of the path of the first or second engagement member is equal to or longer than the path followed by the actuator member 26.

In the particular example of FIG. 2, the first engagement member 14 is rigidly attached to a connecting bar 24 which is slide ably mounted within a housing formed by a rigid connection between the second engagement member 16 and the handle 26. A ratchet mechanism may be provided for transforming motion of the actuator member 20 relative to the handle 26 into a corresponding linear movement of the connecting bar 24. A spring element 22 may be provided for facilitating return of the actuator member 20 after actuation of the actuator member 20. Multiple actuations of the actuator member 20 may be applied in order to achieve a given linear displacement between the first and second engagement members 14 and 16. This arrangement represents just one (particularly convenient) way of implementing the desired functionality of the displacement device. However, it is envisaged that a wide variety of other mechanisms may be employed.

Figure 3:
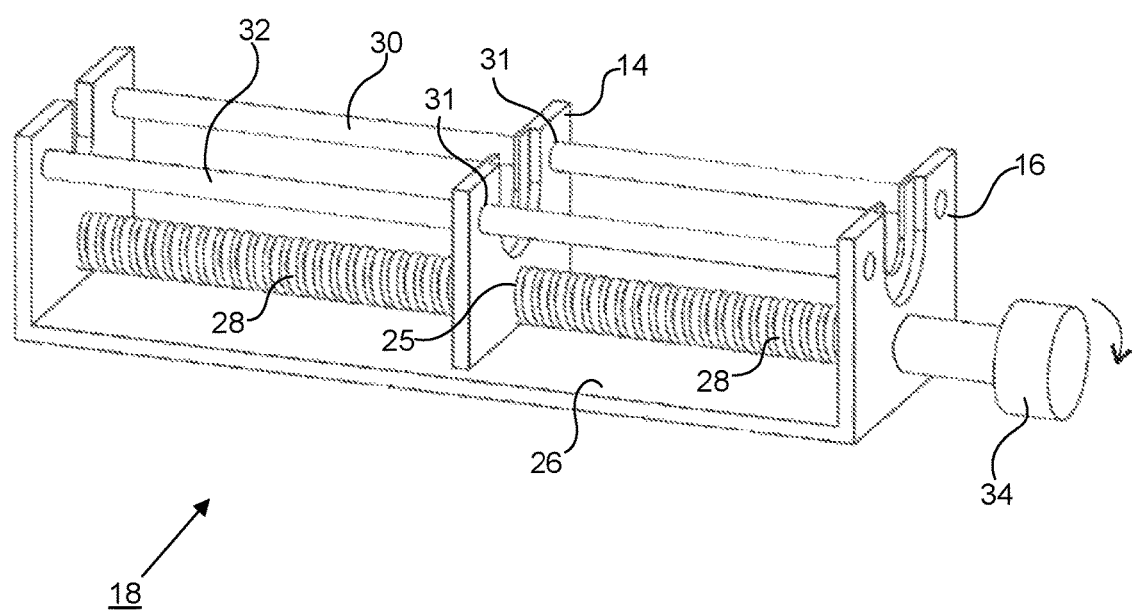
FIG. 3 depicts a stent placement assembly in which the displacement device comprises a threaded bar assembly.

FIG. 3 depicts an alternative configuration for the displacement device 18. In this embodiment, the displacement device 18 comprises a threaded bar 28 mounted rotatably in a frame 26 that is an integral part of or is rigidly attached to a handle 26. One of the first and second anchor members 14 and 16 comprises a threaded orifice 25 (the first engagement member 14 in this example). The threaded bar 28 extends through the orifice 25 and an outer thread of the threaded bar 28 engages with an inner thread of the threaded orifice 25. The anchor member 14 having the threaded orifice 25 is mounted so as to be movable parallel to an axis of rotation of the threaded bar 28 but is constrained so as not to be rotatable about the axis of rotation of the threaded bar 28. In the particular embodiment shown, rotation about the axis of rotation of the threaded bar 28 is prevented by means of stability bars 30 and 32 which are rigidly connected to the frame 26 and are slidably engaged through openings 31 in the first anchor member 14. In this way, rotation of the threaded bar 28 causes linear motion of the first engagement member 14 relative to the second engagement member 16. A gripping device 34 may be provided to allow a user to impart rotation to the threaded bar 28. The pitch of the threads on the threaded bar 28 and/or the radial size of the gripping device 34 may be varied according to the desired sensitivity that is required for the operator. For example, when high precision is required, a relatively fine thread and/or a radially large gripping device 34 may be provided. Conversely, when it is desired to impart quicker motion to the first and second engagement members, a coarser thread and/or smaller gripping device 34 may be provided.

In an embodiment, a kit is provided for use in conjunction with a catheter assembly 1, for example of the type illustrated in FIG. 1. The kit may comprise first and second anchor members which are couplable to proximal ends of the holding catheter and stopper member. In an embodiment of this type, the holding catheter and stopper members may not themselves comprise anchor members. Alternatively or additionally, the catheter assembly 1 may comprise elements which act as anchor members but the kit may provide additional anchor members which improve the connection between the catheter assembly 1 and the displacement device 18. The additional anchor members may comprise washers or similar, for example, which may be mounted onto appropriate parts of the catheter assembly. In an embodiment, the kit further comprises the displacement device itself.

The invention claimed is:

1. A stent placement assembly, comprising:
a holding catheter comprising a longitudinal lumen for receiving a stent, and an output orifice at a distal end;
a stopper member positioned within said longitudinal lumen and moveable longitudinally relative thereto, the stopper member being configured to engage with the stent in order to restrict movement of the stent in a proximal direction;
a first anchor member coupled to the holding catheter at a proximal end thereof;
a second anchor member coupled to the stopper member at a proximal end thereof; and
a displacement device comprising a first engagement member and a second engagement member, the first and second engagement members being configured to engage respectively with the first and second anchor members in such a way that displacement of the first engagement member relative to the second engagement member causes a corresponding displacement between the first and second anchor members, wherein the first and second engagement members are configured to engage detachably with the first and second anchor members, and
the displacement device further comprises:
a handle rigidly connected to one of the first and second engagement members such that the one of the first and second engagement members is prevented from moving relative to the handle; and
a user actuatable displacement mechanism configured to be actuatable by a user while gripping the handle, the actuation being such as to cause displacement of the first engagement member relative to the second engagement member by displacing the other one of the first and second engagement members relative to the handle thereby causing the holding catheter to withdraw in a proximal direction relative to the stopper member and thereby release the stent through the output orifice.

2. The assembly according to claim 1, wherein the user actuatable displacement mechanism comprises an actuator member and a movement transducer for transforming movement of the actuator member imparted by the user into the displacement of the first or second engagement member relative to the handle.

3. The assembly according to claim 2, wherein the displacement of the first or second engagement member follows a path that is different in shape or direction to a path followed by the actuator member.

4. The assembly according to claim 2, wherein the displacement of the first or second engagement member follows a path that is of a different length to a path followed by the actuator member.

5. The assembly according to claim 1, wherein:
the displacement device comprises a threaded bar mounted rotatably in a frame that is an integral part of or is rigidly attached to the handle;
one of the first and second anchor members comprises a threaded orifice through which the threaded bar extends, an outer thread of the threaded bar engaging with an inner thread of the threaded orifice;
the anchor member having the threaded orifice is mounted so as to be movable parallel to the axis of rotation of the threaded bar but not rotatable about a axis of rotation of the threaded bar;
the user actuatable displacement mechanism comprises a gripping device to allow the user to rotate the threaded bar and thereby cause linear movement of the anchor member having the threaded orifice relative to the other anchor member.

6. A kit for facilitating operation of a catheter assembly for deploying a stent that comprises a holding catheter comprising a longitudinal lumen for receiving the stent, the holding catheter having an output orifice at a distal end, and a stopper member positioned within said longitudinal lumen and movable longitudinally relative thereto, the stopper member being configured to engage with the stent in order to restrict movement of the stent in a proximal direction, wherein the kit comprises:
a first anchor member couplable to the holding catheter at a proximal end thereof:
a second anchor member couplable to the stopper member at a proximal end thereof: and
a displacement device comprising a first engagement member and a second engagement member, the first and second engagement members being configured to engage respectively with the first and second anchor members, when coupled to the holding catheter and the stopper member, in such a way that displacement of the first engagement member relative to the second engagement member causes a corresponding displacement between the first and second anchor members, wherein the first and second engagement members are configured to engage detachably with the first and second anchor members, and
the displacement device further comprises:
a handle rigidly connected to one of the first and second engagement member such that the one of the first and second engagement members is prevented from moving relative to the handle; and
a user actuatable displacement mechanism configured to be actuatable by a user while gripping the handle, the actuation being such as to cause displacement of the first engagement member relative to the second engagement member by displacing the other one of the first and second engagement members relative to the handle thereby causing the holding catheter to withdraw in a proximal direction relative to the stopper member and thereby release the stent through the output orifice.

7. A displacement device for facilitating operation of a catheter assembly for deploying a stent, the catheter assembly comprising a holding catheter comprising a longitudinal lumen for receiving the stent, the holding catheter having an output orifice at a distal end, and a stopper member positioned within said longitudinal lumen and moveable longitudinally relative thereto, the stopper member being configured to engage with the stent in order to restrict movement of the stent in a proximal direction, a first anchor member coupled to the holding catheter at a proximal end thereof, and a second anchor member coupled to the stopper member at a proximal end thereof, wherein the displacement device comprises:
a first engagement member and a second engagement member, the first and second engagement members being configured to engage respectively with the first and second anchor members in such a way that displacement of the first engagement member relative to the second engagement member causes a corresponding displacement between the first and second anchor members, wherein the first and second engagement members are configured to engage detachably with the first and second anchor members;

a handle rigidly connected to one of the first and second engagement members such that the one of the first and second engagement members is prevented from moving relative to the handle; and a user actuatable displacement mechanism configured to be actuatable by a user while gripping the handle, the actuation being such as to cause displacement of the first engagement member relative to the second engagement member by displacing the other one of the first and second engagement members relative to the handle thereby causing the holding catheter to withdraw in a proximal direction relative to the stopper member and thereby release the stent through the output orifice.

\* \* \* \* \*